(12) United States Patent
Aaron et al.

(10) Patent No.: US 10,714,227 B2
(45) Date of Patent: Jul. 14, 2020

(54) ROTATING RADIATION SHUTTER COLLIMATOR

(71) Applicant: GEORGETOWN RAIL EQUIPMENT COMPANY, Georgetown, TX (US)

(72) Inventors: Charles Wayne Aaron, Bertram, TX (US); Shuang Cui, Gainesville, FL (US); Michael John Liesenfelt, Austin, TX (US); Paul Daniel Ridgeway, Georgetown, TX (US); James Edward Baciak, Gainesville, FL (US); Jeb Everett Belcher, Georgetown, TX (US)

(73) Assignees: GEORGETOWN RAIL EQUIPMENT COMPANY, Georgetown, TX (US); UNIVERSITY OF FLORIDA RESEARCH FOUNDATION INCORPORATED, Gainesville, FL (US)

( * ) Notice: Subject to any disclaimer, the term of this patent is extended or adjusted under 35 U.S.C. 154(b) by 354 days.

(21) Appl. No.: 15/615,055

(22) Filed: Jun. 6, 2017

(65) Prior Publication Data
US 2017/0352444 A1 Dec. 7, 2017

Related U.S. Application Data

(60) Provisional application No. 62/346,398, filed on Jun. 6, 2016.

(51) Int. Cl.
*A61B 6/06* (2006.01)
*G21K 1/02* (2006.01)
*G21K 1/04* (2006.01)

(52) U.S. Cl.
CPC ............ *G21K 1/043* (2013.01); *G21K 1/02* (2013.01); *G21K 1/04* (2013.01); *G21K 1/046* (2013.01); *A61B 6/06* (2013.01)

(58) Field of Classification Search
CPC . A61B 6/06; G21K 1/02; G21K 1/025; G21K 1/04; G21K 1/043; G21K 1/046
(Continued)

(56) References Cited

U.S. PATENT DOCUMENTS 6,711,236 B2 * 3/2004 Izuhara ................. A61B 6/035
                                                             250/505.1
7,050,544 B2 * 5/2006 Karlsson ................. A61B 6/08
                                                             378/148
(Continued)

*Primary Examiner* — Allen C. Ho
(74) *Attorney, Agent, or Firm* — Parsons Behle & Latimer

(57) ABSTRACT

A shutter for controlling radiation exposure includes a rotatable member. The rotatable member is rotatable between an open position and a closed position. The rotatable member includes a passageway, wherein the passageway is positioned to receive radiation in the open position and is not positioned to receive radiation in the closed position. In the closed position, the rotatable member may substantially block or absorb the radiation. The passageway may collimate the radiation into a beam of radiation. The rotatable member may include a plurality of passageways positioned to receive radiation in the open position. The rotatable member may be rotatable between a plurality of open positions, each open position corresponding to at least one passageway. The open positions may align the source of radiation with different passageways in the rotatable member to form a different beam shape, a different number of beams, a different beam direction, or combinations thereof.

22 Claims, 7 Drawing Sheets

(58) Field of Classification Search
USPC .................................................. 378/147–151
See application file for complete search history.

(56) References Cited

U.S. PATENT DOCUMENTS

| | | | | |
|---|---|---|---|---|
| 7,123,680 B2 * | 10/2006 | Katada | ................... | A61B 6/032 378/16 |
| 7,170,975 B2 * | 1/2007 | Distler | ................... | A61B 6/032 378/147 |
| 7,190,758 B2 * | 3/2007 | Hagiwara | .............. | A61B 6/032 378/7 |
| 7,263,171 B2 * | 8/2007 | Zhang | ..................... | G21K 1/04 250/505.1 |
| 7,330,535 B2 * | 2/2008 | Arenson | ................. | G21K 1/04 378/156 |
| 7,593,510 B2 * | 9/2009 | Rothschild | .............. | G21K 1/04 378/146 |
| 7,831,023 B2 * | 11/2010 | Wedel | ..................... | A61B 6/06 378/148 |
| 8,005,187 B2 * | 8/2011 | Suzuki | ................... | A61B 6/032 378/19 |
| 8,009,807 B2 * | 8/2011 | Petrik | ..................... | G21K 1/04 378/148 |
| 8,064,568 B2 * | 11/2011 | Von Der Haar | ....... | A61B 6/032 378/147 |
| 8,130,901 B2 * | 3/2012 | Muller | .................... | A61B 6/06 378/147 |
| 8,199,884 B2 * | 6/2012 | Junjie | .................... | G21K 1/04 378/150 |
| 8,284,903 B2 * | 10/2012 | Yuan | ........................ | A61B 6/06 378/156 |
| 8,340,246 B2 * | 12/2012 | Kang | ........................ | A61B 6/06 378/146 |
| 8,576,989 B2 * | 11/2013 | Kaminski | ................. | G21K 1/043 378/160 |
| 8,761,338 B2 * | 6/2014 | Safai | .................... | G01N 23/203 378/197 |
| 8,798,230 B2 * | 8/2014 | Cho | ........................ | A61B 6/405 378/19 |
| 8,824,638 B2 * | 9/2014 | Nicholson | ................ | A61B 6/06 378/150 |
| 8,853,636 B2 * | 10/2014 | Perkins | ................ | A61N 5/1042 250/363.1 |
| 8,890,100 B2 * | 11/2014 | Huntzinger | .............. | G21K 1/10 250/503.1 |
| 8,964,942 B2 * | 2/2015 | Dafni | .................... | G01T 1/2985 378/150 |
| 8,983,033 B2 * | 3/2015 | Chen | .................... | G01N 23/203 378/87 |
| 9,014,339 B2 * | 4/2015 | Grodzins | ............. | G01N 23/046 359/233 |
| 9,014,341 B2 * | 4/2015 | Zhang | ..................... | A61B 6/03 378/147 |
| 9,020,103 B2 * | 4/2015 | Grodzins | ............... | G21K 1/046 359/223.1 |
| 9,031,192 B2 * | 5/2015 | Zhao | ...................... | G21K 1/043 378/87 |
| 9,111,656 B2 * | 8/2015 | Schmidt | .................. | G21K 1/04 |
| 9,121,809 B2 * | 9/2015 | Cox | ....................... | G01N 23/04 |
| 9,123,450 B2 * | 9/2015 | Liesenfelt | ................ | G21K 1/04 |
| 9,125,572 B2 * | 9/2015 | Noo | ........................ | A61B 6/027 |
| 9,138,196 B2 * | 9/2015 | Zhu | ........................ | G21K 1/04 |
| 9,161,727 B2 * | 10/2015 | Jenkins | ................... | G21K 1/04 |
| 9,190,182 B2 * | 11/2015 | Mellor | .................... | G01T 1/169 |
| 9,194,827 B2 * | 11/2015 | Kang | ..................... | G21K 1/043 |
| 9,198,626 B2 * | 12/2015 | Heuscher | ............... | A61B 6/032 |
| 9,208,918 B2 * | 12/2015 | Tybinkowski | ........... | G21K 1/02 |
| 9,237,875 B2 * | 1/2016 | Pan | ........................ | A61B 6/06 |
| 9,259,191 B2 * | 2/2016 | Noo | ........................ | G21K 1/02 |
| 9,312,038 B2 * | 4/2016 | Takagaki | ................. | A61B 6/06 |
| 9,332,946 B2 * | 5/2016 | Heuscher | ............... | A61B 6/032 |
| 9,362,013 B2 * | 6/2016 | Pani | ........................ | A61B 6/037 |
| 9,420,981 B2 * | 8/2016 | Baek | ...................... | A61B 6/032 |
| 9,557,284 B2 * | 1/2017 | Vogler | ................. | G01N 23/203 |
| 9,592,014 B2 * | 3/2017 | Melman | ................... | A61B 6/06 |
| 9,775,225 B2 * | 9/2017 | Tamura | ................... | A61B 6/032 |
| 9,786,401 B2 * | 10/2017 | Deprez | ................... | A61B 6/037 |
| 9,820,709 B2 * | 11/2017 | Melman | .................. | A61B 6/5205 |
| 9,978,471 B2 * | 5/2018 | Wang | .................... | G01V 5/0016 |
| 9,980,682 B2 * | 5/2018 | Ahn | ........................ | A61B 6/03 |
| 9,991,014 B1 * | 6/2018 | Gelbart | ................ | A61B 6/4035 |
| 10,123,756 B2 * | 11/2018 | Karch | ..................... | G21K 1/10 |
| 10,153,060 B2 * | 12/2018 | Haunschild | .............. | G21K 1/04 |
| 10,172,573 B2 * | 1/2019 | Öjelund | ................. | A61B 6/032 |
| 10,314,553 B2 * | 6/2019 | Ikhlef | ..................... | A61B 6/032 |
| 10,327,717 B2 * | 6/2019 | Melman | .................. | G21K 1/043 |
| 10,441,230 B2 * | 10/2019 | Proksa | ................... | A61B 6/4429 |
| 10,441,242 B2 * | 10/2019 | Kim | ........................ | A61B 6/4085 |
| 10,541,061 B2 * | 1/2020 | Wang | ..................... | A61B 6/035 |

* cited by examiner

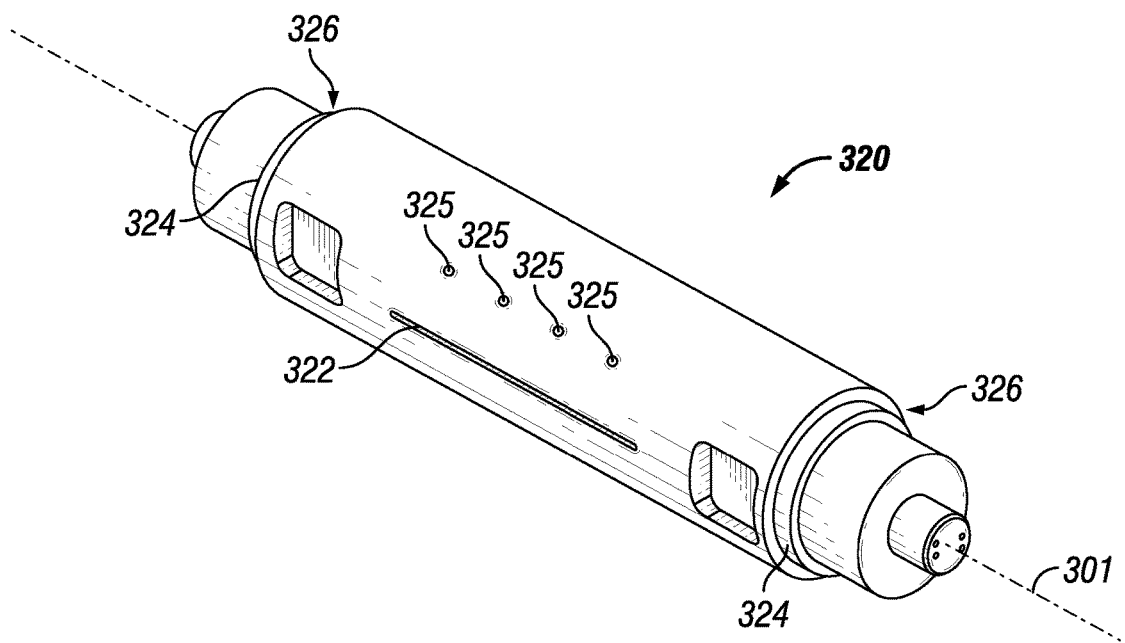
FIG. 10
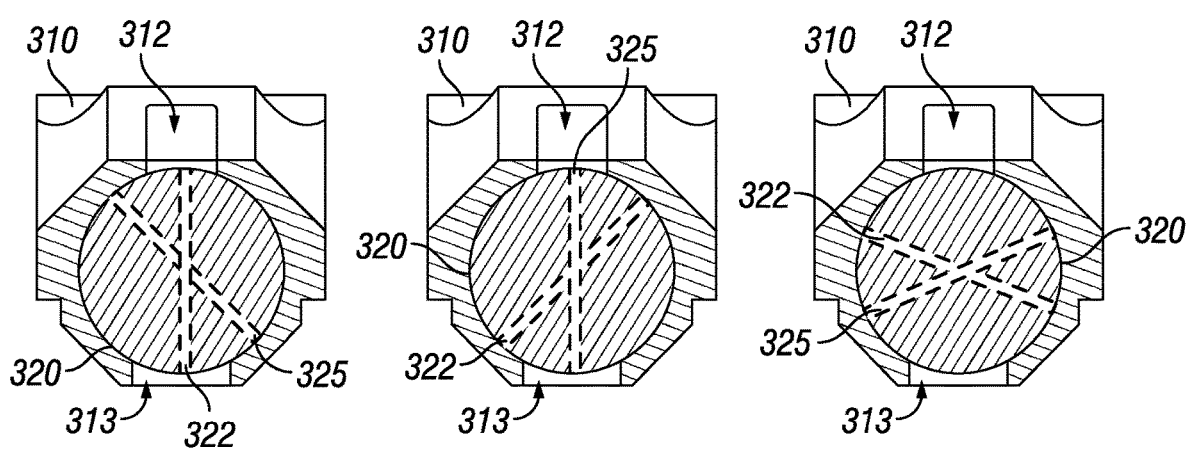
FIG. 11A  FIG. 11B  FIG. 11C

ROTATING RADIATION SHUTTER COLLIMATOR

CROSS REFERENCE TO RELATED APPLICATIONS

The present application claims the benefit of priority under 35 U.S.C. § 119 to U.S. Provisional Application No. 62/346,398, filed Jun. 6, 2016, entitled "ROTATING X-RAY SHUTTER COLLIMATOR," the disclosure of which is incorporated herein by reference in its entirety.

BACKGROUND

Field of the Disclosure

The embodiments described herein relate to systems and methods for selectively controlling exposure to a radiation source. More particular, the embodiments described herein relate to a rotating shutter and methods for selectively controlling the exposure of radiation to a target.

Description of the Related Art

Applications throughout many fields utilize radiation to assess, inspect or examine the internal regions of an object or target. The radiation can be in the form of X-ray, gamma rays, neutron rays, or other energy forms which tend to penetrate beyond the surface of material of different densities. Radiation energy travels in a straight line and loses energy as it travel through material interacting with the material's atoms. Each time radiation strikes an atom of a material it either passes through, is absorbed, or is scattered as a result of the collision. In any case, the intensity of the radiation is reduced by each atom it encounters. However, the amount of energy reduction and how much is scattered, absorbed, or passes straight through the target is dependent on the type of radiation and atomic properties of the material.

When materials are used to contain radiation it is often referred to as radiation shielding, or simply shielding. It may be desirable that radiation energy be controlled such that the radiation is released onto an object and prevented from being released onto another object, or a different portion of the same object. One example is when utilizing an X-ray source to create an X-ray scan of an object. It may be desirable for a radiographer to expose the target for a specific amount of time and protect the target and surroundings from the radiation at other times. Radioactive sources may emit radiation all of the time so it may be desirable to contain the radiation when it is undesirable to expose a target. In contrast, if the radiation is created with an X-ray tube, the radiation can simply be turned on and off. However, it takes time for the X-ray tube to warm-up and the longevity of the X-ray tube may be promoted if it is not repeatedly turned on and off. Therefore, it may be desirable that it be turned on and left on during the duration of a normal operation, and that the radiation be contained while exposure is not desired. Additionally, it may be desirable to limit exposure to a certain area or in a particular pattern.

SUMMARY

The present disclosure is directed to a system and method for selectively controlling the exposure to a radiation source that overcomes and/or mitigates some of the problems and disadvantages discussed above.

The embodiments described herein contain or reduce exposure to radiation from a radiation source when in a closed position and can be selectively opened to expose a target to radiation from the radiation source. The embodiments may be selectively opened by selectively rotating a portion of a shutter. Some embodiments may shape the radiation from the radiation source into predetermined patterns or direct radiation to predetermined areas when selectively opened.

An embodiment of a shutter includes a rotatable member with at least one passageway. The passageway allows radiation from a radiation source to pass through the rotatable member when the rotatable member is oriented in an open position. In the open position, the passageway may be in alignment with approximately the center point of the radiation source. The shutter may include a body. The rotatable member may be mounted on or within the body. The body may be configured to house the rotatable member. The rotatable member may be rotatably mounted in the body in such a fashion that it is allowed to rotate on one axis, such that at one point in its rotation the passageway in the rotatable member is aligned with the radiation source. As the rotatable member rotates in either direction the entry point of the passageway moves away from the source of radiation such that the non-passageway portion of the rotatable member absorbs or blocks the radiation from escaping beyond the rotatable member and the body. Additional rotation may align the source of radiation with a different passageway in the rotatable member to form a different beam shape, a different number of beams, a different beam direction, or combinations thereof. The cross-sectional thickness of the rotatable member in the closed position may be such that any radiation that passes through this thickness of the chosen material is reduced to safe continuous exposure levels, such as not to exceed 2 millirem per hour.

The rotatable member may be comprised of a material that substantially blocks or absorbs the form of radiation being utilized. The body may also be a material that substantially blocks or absorbs the form of radiation being utilized. For example, the rotatable member may comprise a lead or tungsten alloy and the radiation source may be X-rays because these extremely high density metals block X-rays very well. As used herein, substantially blocks or absorbs means reducing the radiation to safe continuous exposure levels for that type of radiation, such as not to exceed 2 millirem per hour. Safe exposure levels may be established by a regulatory agency, such as the Nuclear Regulatory Commission.

The rotatable member may be positioned within the body with a clearance region therebetween. A profile of the clearance region is configured to provide multiple points of scatter for scattered radiation energy. The profile of the clearance region may be a curved or stepped path such that any scattered radiation energy has multiple points of scatter and may essentially lose all energy, such as to safe continuous exposure levels, before it can exit out the ends of the shutter. The clearance region may not be a straight line from the entry point of the passageway to the ends of the rotatable member, where a bearing or sleeve may be located. If the profile were a straight line, the radiation could escape after only one point of scatter, which may still be at much too high of an energy to be released in an undesired direction. The body may comprise a plurality of body pieces to facilitate positioning the rotatable member within the assembled body. The body pieces may be configured to mate with other body pieces to provide multiple points of scatter for scattered radiation energy. The interfaces between the body pieces may be stepped.

The body may be configured to accommodate additional shielding which surrounds the radiation source. The radiation source may be housed in a structure which acts as shielding such that radiation can only escape in a designated area. The body of the shutter may mount to the housing of the radiation source such that backscattered radiation cannot escape between the radiation source and the body of the shutter. A driving mechanism may control the rotational movement of the rotatable member. The driving mechanism may include a motor or a linkage connected to the rotatable member. The driving mechanism may include a double acting pneumatic cylinder configured to rotate the rotatable member between the open and closed positions. An air supply may provide pressurized gas to the double acting pneumatic cylinder. The pneumatic cylinder may include a control valve configured to position the rotatable member in the closed position in the event of a loss of power or pressure. The driving mechanism may utilized stored energy, such as a spring, to position the rotatable member in the closed position in the event of a loss of power or pressure. The shutter system may include a controller for operating the driving mechanism. For example, the controller may monitor systems associated with radiography inspection and operate the shutter accordingly, such as with an interlock trigger. Various interlock triggers may be used, such as manual and auto-switching triggers. Auto-switching triggers may include encoder triggers and GPS triggers. The various interlock triggers may include a position interlock, a key interlock, an inertial interlock, a speed interlock, or other interlock triggers as may be appreciated by a person of ordinary skill having the benefit of this disclosure.

An embodiment of a shutter for selectively controlling radiation exposure includes a body and a rotatable member. The rotatable member is rotatably connected to the body and is rotatable between an open position and a closed position. The open position permits radiation to pass through the rotatable member and the closed position substantially blocks or absorbs the radiation that would pass through the rotatable member in the open position.

The rotatable member may be configured to collimate the radiation into at least one beam of radiation in the open position. The at least one beam of radiation may be a plurality of beams of radiation. The rotatable member may include a radiation inlet, a radiation outlet, and a passageway extending from the radiation inlet to the radiation outlet. The radiation inlet is positioned to receive radiation when the rotatable member is in the open position. The passageway may be shaped to form the radiation into a fan beam. The passageway may be shaped to form the radiation into a pencil beam.

The rotatable member may include at least one second radiation inlet, at least one second radiation outlet, and at least one second passageway extending from the at least one second radiation inlet to the at least one second radiation outlet. The radiation inlet and the at least one radiation outlet may be positioned to receive radiation when the rotatable member is in the open position. The at least one radiation inlet may be a plurality of radiation inlets. The at least one radiation outlet may be a plurality of radiation outlets. The rotatable member may be rotatable to a second open position. The radiation inlet may be positioned to receive radiation when the rotatable member is in the open position and the at least one second radiation inlet may be positioned to receive radiation when the rotatable member is in the second open position. The body may include a body radiation inlet, a body radiation outlet, and a radiation source profile positioned adjacent the body radiation inlet and configured to receive an exterior surface of a radiation source. At least one of the body radiation inlet or body radiation outlet may include a cover that is transmissive to a portion of radiation. The rotatable member may be positioned within the body with a clearance region therebetween. The clearance region being may be configured to provide multiple points of scatter for scattered radiation energy.

An embodiment of a method of selectively controlling radiation exposure includes receiving radiation into a shutter having a rotatable member and rotating the rotatable member between an open position and a closed position. The open position permits radiation to pass through the rotatable member. The closed position substantially blocks or absorbs the radiation.

The method may include collimating the radiation into at least one beam of radiation when the rotatable member is in the open position. At least one beam of radiation may be a fan beam. At least one beam of radiation may be a pencil beam. The method may include rotating the rotatable member to a second open position and collimating the radiation into at least one second beam of radiation when the rotatable member is in the second open position.

An embodiment of a shutter for selectively controlling radiation exposure includes a rotatable member. The rotatable member has at least one passageway, a closed position, and at least one open position. The rotatable member is rotatable between the closed position and at least one open position. The at least one passageway is not positioned to receive radiation when the rotatable member is in the closed position. The at least one passageway is positioned to receive radiation when the rotatable member is in the at least one open position.

The at least one passageway may be configured to collimate the radiation into at least one beam of radiation. The at least one passageway may be a plurality of passageways including a first passageway and a second passageway. The at least one open position may include an open position that permits radiation to simultaneously pass through the first passageway and the second passageway. The at least one open position may include a first open position and a second open position. The rotatable member may be rotatable between the first open position and the second open position. The first open position permits radiation to pass through the first passageway. The second open position permits radiation to pass through the second passageway.

BRIEF DESCRIPTION OF THE DRAWINGS

FIG. 10 shows an embodiment of a rotatable member.

FIG. 11A shows an end cross-sectional view of the embodiment of FIG. 10 rotated to a first open position within a body.

FIG. 11B shows an end cross-sectional view of the embodiment of FIG. 10 rotated to a second open position within a body.

FIG. 11C shows an end cross-sectional view of the embodiment of FIG. 10 in a closed position within a body.

Figure 1:
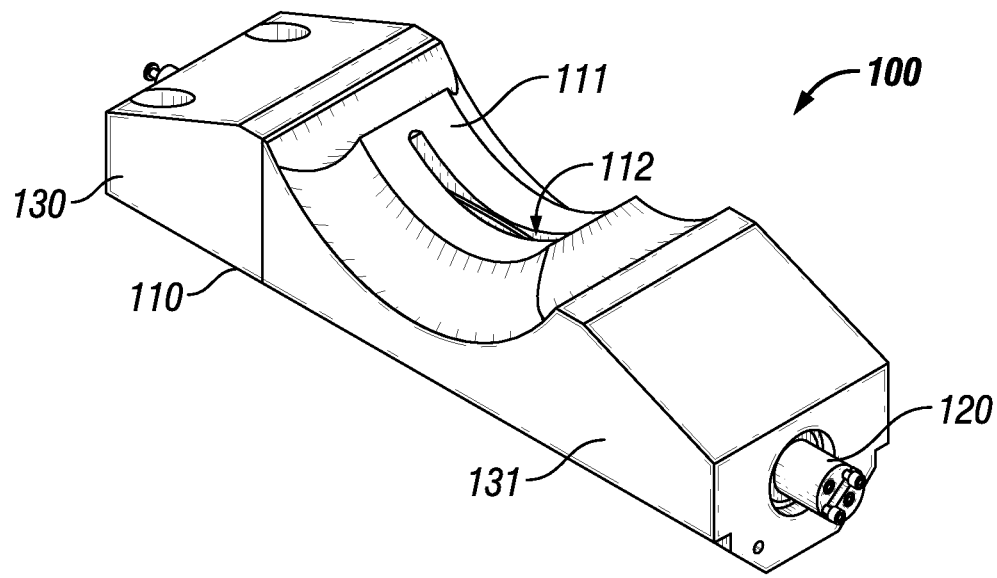
FIG. 1 shows an embodiment of a shutter having a body and a rotatable member.

While the disclosure is susceptible to various modifications and alternative forms, specific embodiments have been shown by way of example in the drawings and will be described in detail herein. However, it should be understood that the disclosure is not intended to be limited to the particular forms disclosed. Rather, the intention is to cover all modifications, equivalents and alternatives falling within the scope of the disclosure as defined by the appended claims.

DESCRIPTION

Figure 2:
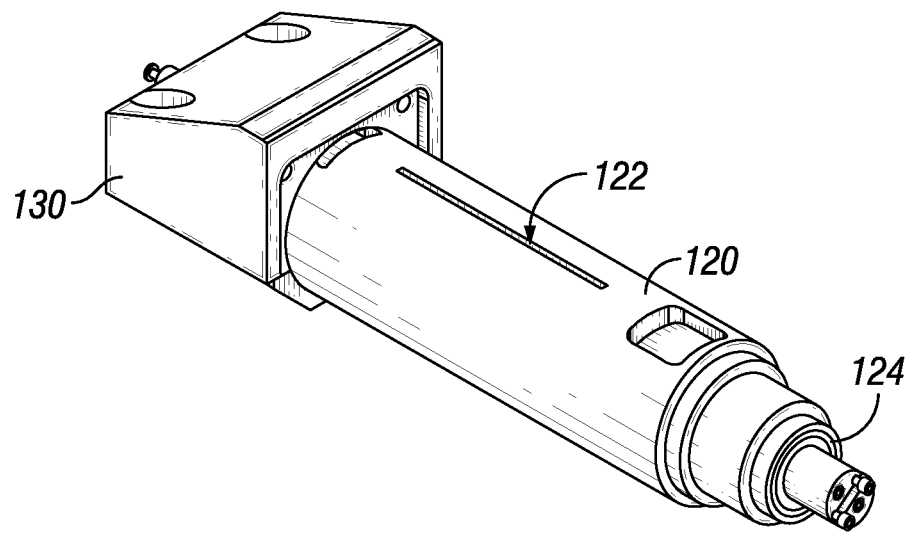
FIG. 2 shows the embodiment of FIG. 1 with a portion of the body removed to better show the rotatable member.
Figure 3:
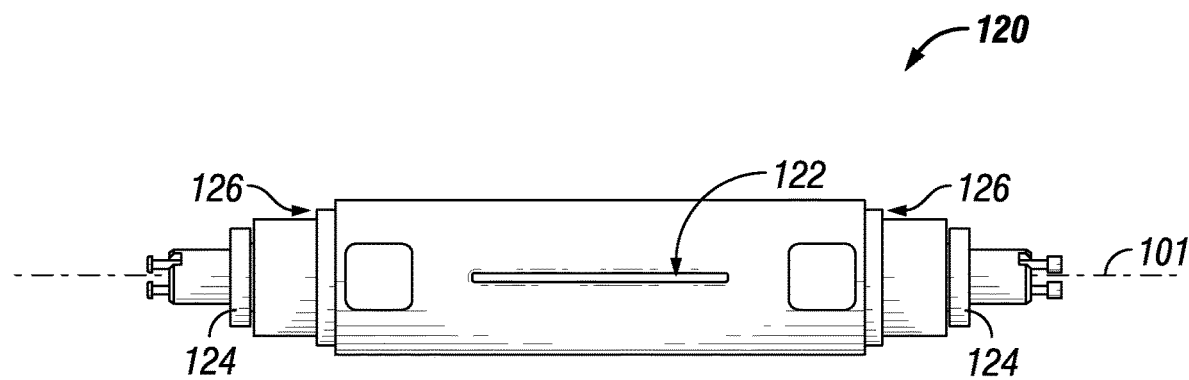
FIG. 3 shows a top view of an embodiment of a rotatable member.
Figure 4:
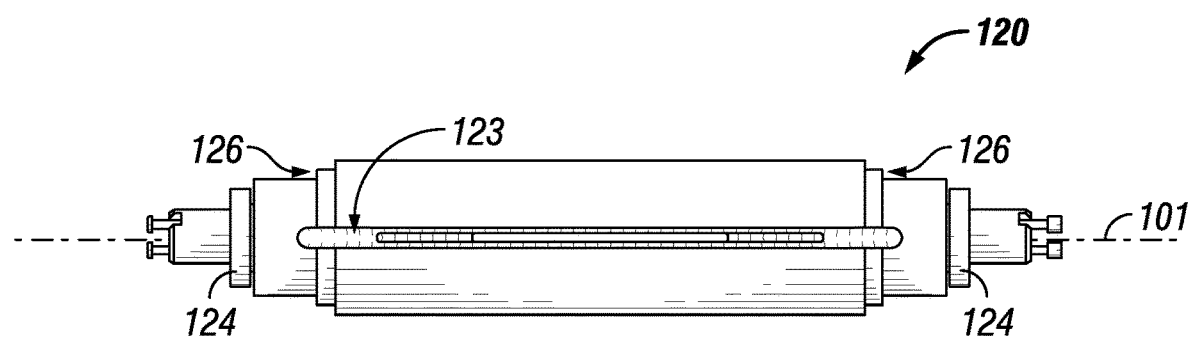
FIG. 4 shows a bottom view of the embodiment of FIG. 3.

FIG. 1 shows an embodiment of a shutter 100 having a body 110 and a rotatable member 120 (best seen in FIGS. 2-4). The rotatable member 120 may be a cylindrical member. The body 110 may comprise a plurality of body pieces 130, 131. The body 110 includes a radiation inlet 112 configured to receive energy from a radiation source 10 (shown in FIG. 7) when the shutter 100 is positioned between a target to be radiated and the radiation source 10. The shutter 100 is configured to selectively control exposure of a target or object to radiation from the radiation source 10 (shown in FIG. 7). By way of example, the radiation source 10 may be an x-ray tube, neutron ray source, or gamma ray source. The radiation source 10 is configured to emit a radiation field from an area on the outside surface of the radiation source 10, such as the bottom side portion of an x-ray tube. The body 110 of the shutter 100 includes a radiation source profile 111 configured to mate with an outside surface of a radiation source 10. The connection between the radiation source 10 and the body 110 may prevent backscattered radiation from being transmitted therebetween. The radiation source profile 111 may be configured to position the radiation source 10 such that emitted radiation is aligned with the radiation inlet 112 in the body 110 and a radiation inlet 122 (shown in FIG. 2) in the rotatable member 120 when the rotatable member 120 is oriented in an open position. A driving mechanism (not shown) may be mechanically connected to the rotatable member 120 to provide rotational motion. The driving mechanism may include a controller configured to operate the shutter 100. The controller may be manually operated or may monitor systems associated with radiography inspection and operate the shutter 100 accordingly. For example, the controller may be logically connected to an interlock trigger that actuates the rotatable member 120 of the shutter 100 between its open and closed positions.

FIG. 2 shows the embodiment of FIG. 1 with body piece 131 of the body 110 removed to more clearly show the rotatable member 120 in the open position. In the open position, at least a portion of the radiation from the radiation source 10 (shown in FIG. 7) passes through the radiation inlet 112 in the body 110 (shown in FIG. 1) and into the radiation inlet 122 of the rotatable member 120. The rotatable member 120 may include sleeves or bearings 124 to rotatably support the rotatable member 120 within the body 110. The body 110 and rotatable member 120 may be formed of a lead alloy with up to approximately 5% antimony, to add rigidity and hardness.

FIG. 3 shows a top view the rotatable member 120. FIG. 4 shows a bottom view of the rotatable member 120. The rotatable member 120 is rotatable about an axis of rotation 101 along the length of the rotatable member 120. Sleeves or bearings 124 may be positioned along the rotatable member 120 to support the rotatable member 120 within the body 110 (shown in FIG. 1) while still allowing rotation motion of the rotatable member 120 along its axis of rotation 101. The rotatable member 120 includes a passageway having a radiation inlet 122 configured to receive radiation from a radiation source 10 and a radiation outlet 123 disposed on an opposite side of the rotatable member 120. The passageway may be configured to form a collimated beam of radiation.

As shown in the embodiment of FIGS. 3 and 4, the passageway in the rotatable member 120 may have two parallel sides spaced relatively closely and extending along a portion of the length of the rotatable member 120. The two parallel sides of the passageway extend from the radiation inlet 122 to the radiation outlet 123. The passageway may include two other sides 121 (shown in FIG. 8B) at an angle to each other and extending from the radiation inlet 122 to the radiation outlet 123. The shape of the passageway of the rotatable member 120 may collimate X-rays from the radiation source 10 to form a triangular (fan beam) shaped plane of X-rays, with the top point of the triangle located at the center of the X-ray source and the two outer edges of the triangle determined by the angle of the two other sides 121 (shown in FIG. 8B) of the passageway in the rotatable member 120. The spacing of the two parallel sides of the passageway in the rotatable member 120 may be selected to determine the thickness of the plane of radiation that is emitted from the radiation outlet 123 of the rotatable member 120. The plane of radiation may be selected such that only a narrow cross-section of a target is radiated and scanned at any given moment, thus allowing the inspection or examination of one narrow cross-section at a time. The target to be inspected may be translated with respect to the radiation system, or the radiation system may be translated with respect to the target, to get a complete examination of the entire target, as a set of multiple scans each representing one cross-section. The sides of the passageway may be configured to form other shapes, such as circles and cones, as would be appreciated by one of ordinary skill in the art having the benefit of this disclosure.

Figure 8A:
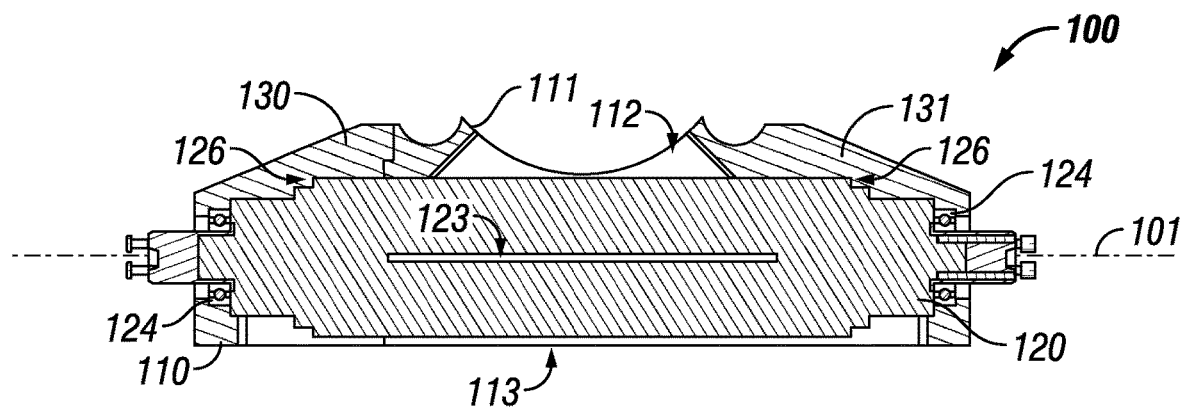
FIG. 8A shows a cross-sectional view of an embodiment of a shutter in a closed position.
Figure 8B:
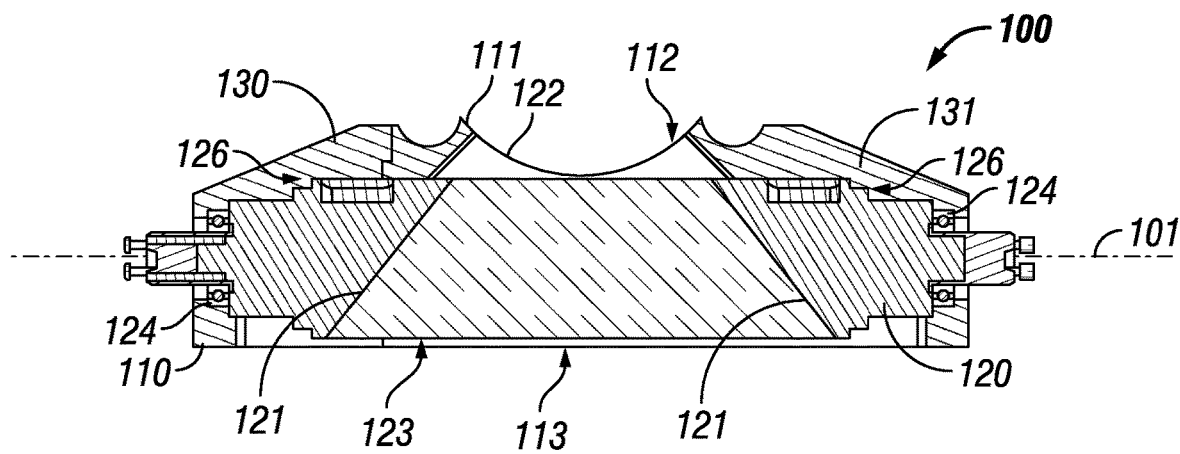
FIG. 8B shows a cross-sectional view the embodiment of FIG. 8A in an open position.

The rotatable member 120 may have a profile with stepped shoulders 126 to increase the points of scatter for scattered radiation energy within a clearance region between the rotatable member 120 and body 110 (shown in FIGS. 8A and 8B). Other clearance region profiles, such as a curved path, are possible as may be appreciated by one of ordinary skill in the art having the benefit of this disclosure.

Figure 5:
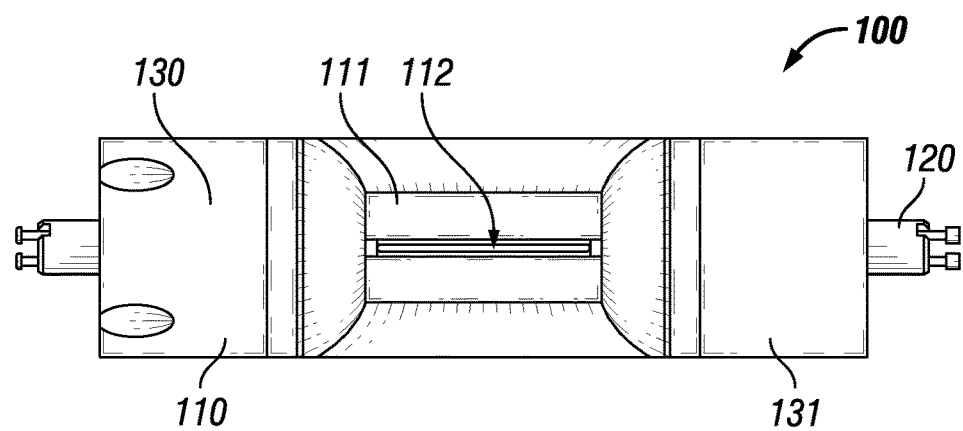
FIG. 5 shows a top view of an embodiment of a shutter.
Figure 6:
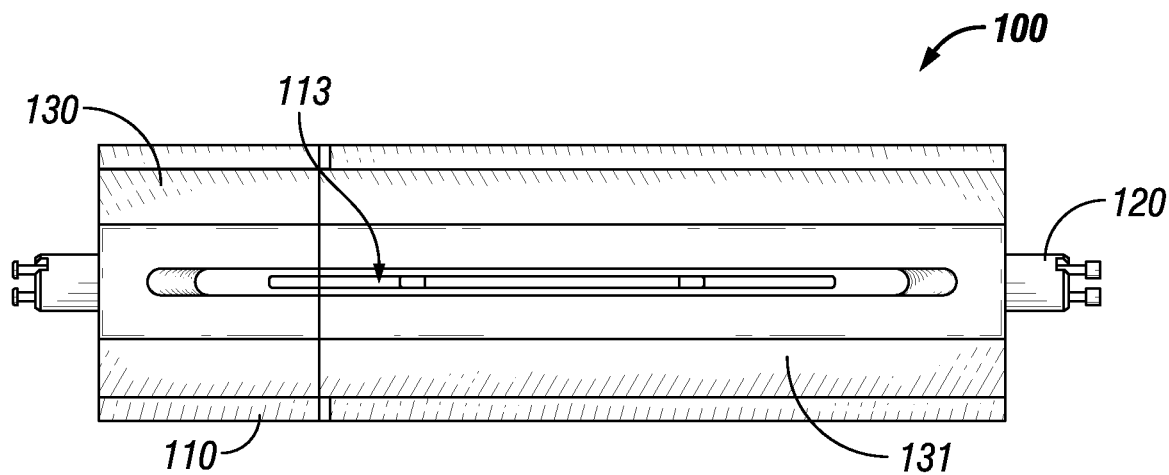
FIG. 6 shows a bottom view of an embodiment of a shutter.

FIG. 5 shows a top view of the shutter 100. FIG. 6 shows a bottom view of the shutter 100. The body 110 of the shutter 100 includes a radiation source profile 111 configured to mate with an outside surface of a radiation source 10, such as a housing of the radiation source 10 (shown in FIG. 7). The body 110 may comprise body pieces 130, 131. During assembly, the rotatable member 120 may be connected to or positioned within body piece 130. Body piece 131 may then be connected to body piece 130 to house the rotatable member 120 within the body 110. The body 110 includes a radiation inlet 112 and a radiation outlet 113. The radiation inlet 112 is configured to receive radiation from the radiation source 10 (shown in FIG. 7). The radiation outlet 113 of the body 110 is configured to receive radiation from the radiation outlet 123 (shown in FIG. 4) of the passageway of the rotatable member 120 when the rotatable member 120 is in the open position. The shape of the radiation outlet 113 of the body 110 may be configured to pass all of, or at least a portion of, the radiation plane received from radiation outlet 123 of the passageway of the rotatable member 120. A driving mechanism (not shown) is operable to adjust the orientation of the passageway of the rotatable member 120 with respect to the radiation inlet 112 and outlet 113 of the body 110.

Figure 7:
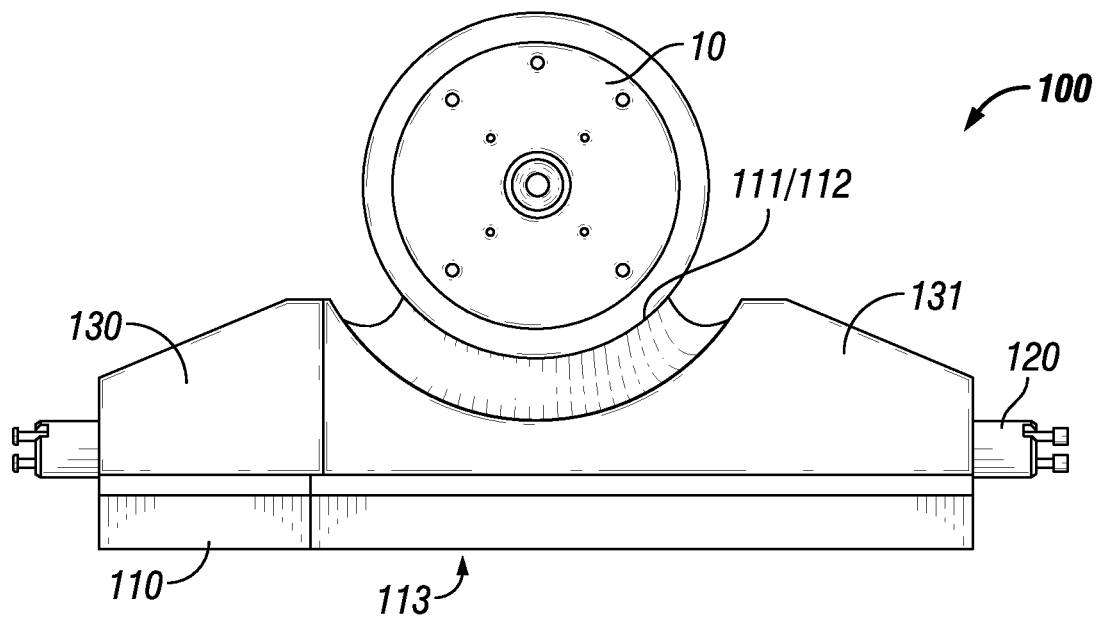
FIG. 7 shows a side view of an embodiment of a shutter connected to a radiation source.

FIG. 7 shows a side view of shutter 100 with the rotatable member 120 rotatably disposed within the body 110 via bearings 124 (shown in FIGS. 8A and 8B). The body 110 includes body pieces 130, 131 that interconnect once the rotatable member 120 has been placed within. A radiation source profile 111 of body 110 is mated with an outside surface of a radiation source 10, such as a housing of the radiation source 10, and radiation from radiation source 10 is directed through the radiation inlet 112 (best shown in FIGS. 8A and 8B) of the body 110 of the shutter 100. The radiation may be cone shaped radiation. Backscattered radiation may be prevented from exiting the shutter 100 between the connection at the radiation source profile 111 of the body 110 and the radiation source 10. In some embodiments, backscattered radiation is substantially blocked or absorbed by the connection between the radiation source profile 111 and the radiation source. The orientation of the rotatable member 120 is selectively controlled to permit or inhibit radiation from passing through the shutter 100. A target may be positioned opposite the radiation source 10 to selectively receive radiation passed through the shutter 100.

In FIGS. 8A and 8B, the radiation source 10 has been removed for illustration purposes and the shutter 100 has been shown in a side cross-sectional view along the axis of rotation of the rotatable member 120. The body pieces 130, 131 are mated to form the body 110. The interface between body piece 130 and body piece 131 is configured to provide multiple points of scatter for scattered radiation energy, such as the stepped interface as shown. FIG. 8A shows the shutter 100 with the rotatable member 120 in a closed position. In the closed position, radiation from radiation source 10 is received through the radiation inlet 112 of the body 110. However, the orientation of the rotatable member 120 prevents radiation from being received into the radiation inlet 122 (shown in FIG. 8B) of the passageway of the rotatable member 120. The radiation may be at least partially absorbed by the rotatable member 120. The radiation may be at least partially absorbed by the body 110. Incident radiation that may exit the shutter 100 while the rotatable member 120 is in the closed position is reduced to safe continuous exposure levels, such as not to exceed 2 millirem per hour. The material of the body 110 and the rotatable member 120 may absorb all of the radiation.

Backscattered radiation may be inhibited from exiting the shutter 100 through radiation inlet 112 of the body 110 via a tight connection between the radiation source profile 111 of body 110 and the radiation source 10. The clearance region between the rotatable member 120 and body 110, shown as including stepped shoulders 126 on the rotatable member 120, provides multiple points of scatter for scattered radiation energy. In some embodiments, profiles and steps may be positioned on an interior portion of the body 110 to form a clearance region, as may be appreciated by a person of ordinary skill having the benefit of this disclosure. The scattered radiation energy may essentially lose all energy before it can exit near the bearings 124 and be reduced to safe continuous exposure levels, such as not to exceed 2 millirem per hour.

FIG. 8B shows a cross-section view of the shutter 100 with the rotatable member 120 in an open position. A driving mechanism (not shown) and controller may be used to selectively rotate the rotatable member 120 from the closed position to the open position. In the open position, radiation from radiation source 10 is received through the radiation inlet 112 of the body 110. Radiation inlet 122 of rotatable member 120 is substantially aligned with the radiation inlet 112 of the body 110. In addition, radiation inlet 122 of rotatable member 120 may be substantially centered on the radiation field emitted from radiation source 10. As shown, the width of the radiation inlet 122 of the rotatable member 120 may be smaller than the width of the radiation inlet 112 of the body 110. Radiation passes into the passageway of the rotatable member 120 via radiation inlet 122. Opposing sides 121 of the passageway extend from the radiation inlet 122 to the radiation outlet 123 of the rotatable member 120 at an angle with respect to each other. The shape of the passageway of the rotatable member 120 collimates radiation from the radiation source 10 with the outer edges of the collimated beams corresponding to the angle of the opposing sides 121 of the passageway in the rotatable member 120. The collimated beam passes out of the radiation outlet 123 of the rotatable member 120 and through the radiation outlet 113 of the body 110 and towards a target to be radiated. Backscattered radiation may be inhibited from exiting the shutter 110 through the clearance region between the rotatable member 120 and body 110 and the connection between the radiation source profile 111 of body 110 and the radiation source 10, as described above. When radiating a target, rotatable member 120 may be rotated between the open and closed positions to selectively radiate portions of the target or reduce exposure levels.

Figure 9:
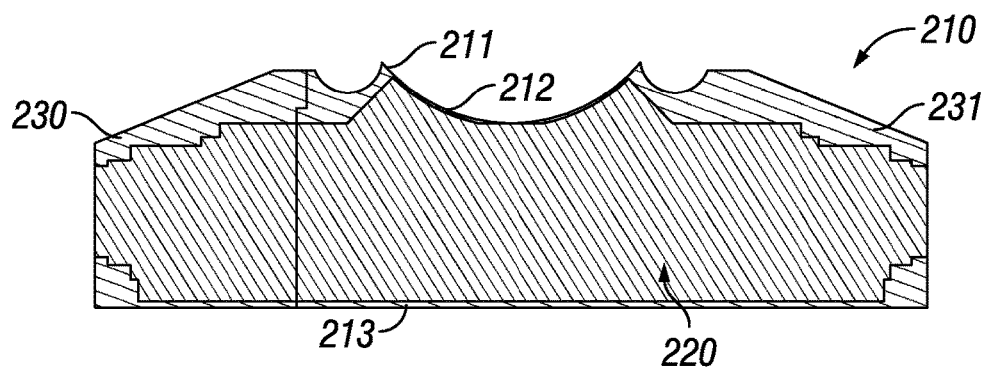
FIG. 9 shows a cross-sectional view of an embodiment of a body.

FIG. 9 shows a cross-sectional view of an embodiment of a body 210. The body 210 includes a cavity 220 configured to receive a rotatable member. The body 210 may comprise body pieces 230, 231 that interconnect once a rotatable member has been placed within. The interface between body piece 230 and body piece 231 is configured to provide multiple points of scatter for scattered radiation energy, such as the stepped interface as shown. The body 210 of the shutter 200 includes a radiation source profile 211 configured to mate with an outside surface of a radiation source. The connection between the radiation source and the body 210 may prevent backscattered radiation from being transmitted therebetween. The body 210 includes a radiation inlet 212 and a radiation outlet 213. The radiation inlet 212 may include an integral cover as shown. The radiation outlet 213 may include a cover as shown. Alternatively, the cover(s) may be connected to the body 210 over an otherwise open radiation inlet or radiation outlet.

The cover inhibits the introduction of foreign objects, such as dust, into the body 210. For example, the cover on the radiation inlet 212 may prevent debris from entering the body 210 when the body 210 is disconnected from a radiation source. Also for example, the cover on the radiation outlet 213 may prevent debris from entering the body 210 when the body 210 is in use, such as when traveling along railroad tracks, roadways, or an inspection line. The cover may comprise a minimal thickness and/or material that is highly transmissive to radiation from the radiation source. The cover may absorb a portion of the radiation passing through the rotatable member while also transmitting a portion of radiation with sufficient levels to perform inspection of a target. The portion of radiation transmitted through the cover may exceed safe continuous exposure levels. The cover may filter low levels of radiation. In operation, radiation is received thought the radiation inlet 212 and selectively passed to the radiation outlet 213, depending on the position of a rotatable member disposed within the cavity 220. In other embodiments, a cover may be integral to a passageway of a rotatable member. The passageway extends through the rotatable member between a radiation inlet and a radiation outlet. The passageway may extend only partially through the rotatable member to form an integral cover.

FIG. 10 shows an embodiment of a rotatable member 320 configured to selectively form a fan beam or a plurality of pencil beams. The rotatable member 320 may include sleeves or bearings to rotatably support the rotatable member 320 within a body 310 (shown in FIGS. 11A-C). The body 310 and rotatable member 320 may be formed of a lead alloy with up to approximately 5% antimony, to add rigidity and hardness. The rotatable member 320 is rotatable about an axis of rotation 301 along the length of the rotatable member 320. The rotatable member 320 is rotatable between at least a first open position, a second open position, and a closed position. The rotatable member 320 may have a profile 326 with stepped shoulders 324 to increase the points of scatter for scattered radiation energy within a clearance region between the rotatable member 320 and the body 310. The rotatable member 320 includes a first passageway 322 having a radiation inlet configured to receive radiation from a radiation source and a radiation outlet disposed on an opposite side of the rotatable member 320. The first passageway 322 may be configured to form a collimated beam of radiation. The first passageway 322 may be configured to form a fan beam.

The rotatable member 320 includes a plurality of second passageways 325. Each of the second passageways 325 has a radiation inlet configured to receive radiation from a radiation source and a radiation outlet disposed on an opposite side of the rotatable member 320. The plurality of second passageways 325 may be configured to form collimated beams of radiation. The plurality of second passageways 325 may be configured to form a plurality of pencil beams. The inlet of the first passageway 322 is circumferential separated from the inlets of the second passageways 325. For example, the first passageway 322 may be positioned 40 degrees rotation from the second passageways.

Figure 12A:
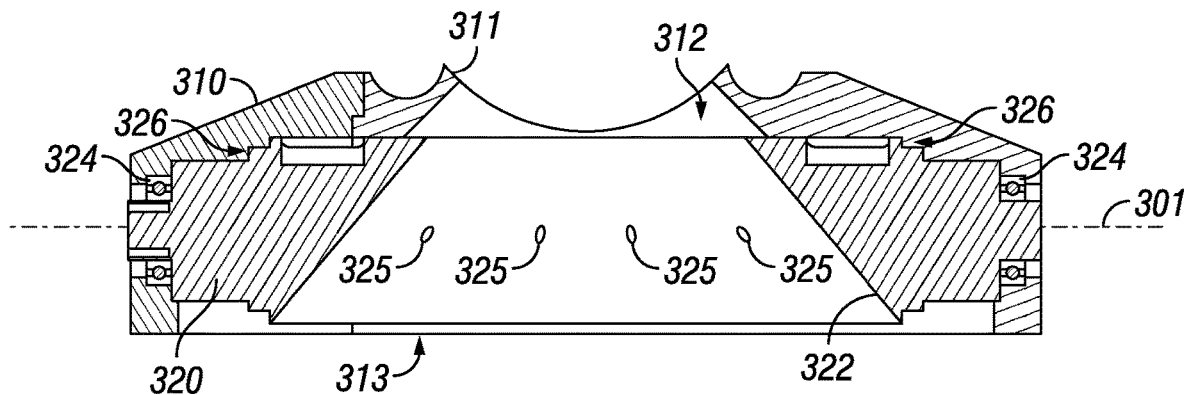
FIG. 12A shows a side cross-sectional view of the embodiment of FIG. 10 rotated to the first open position within a body.
Figure 12B:
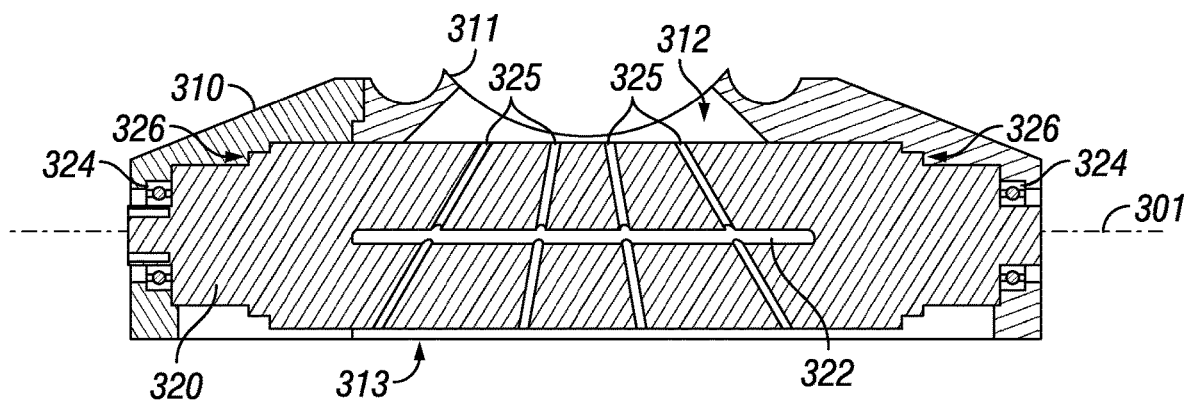
FIG. 12B shows a side cross-sectional view of the embodiment of FIG. 10 rotated to the second open position within a body.
Figure 12C:
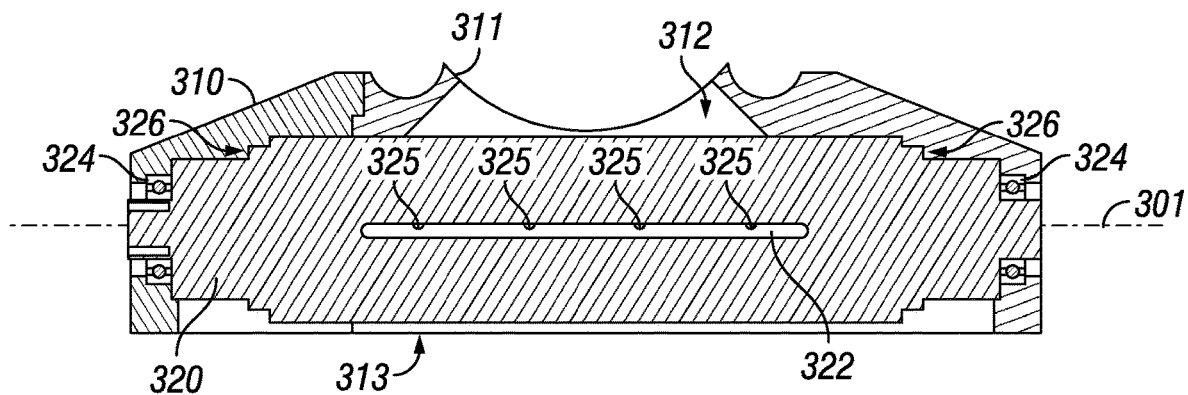
FIG. 12C shows a side cross-sectional view of the embodiment of FIG. 10 rotated to the closed position within a body.

FIGS. 11A-C show an end cross-sectional view of the rotatable member 320 within the body 310 with the rotatable member 320 in different positions. FIGS. 12A-12C show side cross-sectional views of the rotatable member 320 within the body 310. The body 310 includes a radiation inlet 312 and a radiation outlet 313. The radiation inlet 312 is configured to receive radiation from a radiation source (not shown in FIGS. 11A-12C). The radiation outlet 313 of the body 310 may pass all of, or at least a portion of, the radiation received from the rotatable member 320 to a target positioned opposite from the radiation source.

FIGS. 11A and 12A show the rotatable member 320 in the first open position. In the first open position, the radiation inlet of the first passageway 322 is positioned to receive radiation through the radiation inlet 312 of the body 310. Radiation from a radiation source passes though the radiation inlet 312 of the body 310 and into the first passageway 322 where it is formed into a first beam shape. The first beam shape may be a fan beam. The first beam shape is then passed through the radiation outlet 313 of the body 310 and toward a target to be irradiated.

FIGS. 11B and 12B show the rotatable member 320 in the second open position. The rotatable member 320 is rotated from the first open position to the second open position. By way of example, the rotatable member 320 might be rotated 40 degrees about axis 301 from the first open position to the second open position. In the second open position, the radiation inlets of the second passageways 325 are positioned to receive radiation from the radiation inlet 312 of the body 310. Radiation from a radiation source passes though the radiation inlet 312 of the body 310 and into the inlets of the second passageways 325 where it is formed into a plurality of second beam shapes. The second beam shapes may be pencil beams. The pencil beams are then passed through the radiation outlet 313 of the body 310 and toward a target to be irradiated.

FIGS. 11C and 12C show the rotatable member 320 in the closed position. The rotatable member 320 is rotated from the first open position or the second open position to the closed position. By way of example, the rotatable member 320 might be rotated 40 degrees about axis 301 from either the first open position or the second open position to the closed position. In the closed position, the cross-sectional thickness of the rotatable member 320 between the radiation inlet 312 and the radiation outlet 313 may be such that any radiation that passes through this thickness of the chosen material is reduced to safe continuous exposure levels, such as not to exceed 2 millirem per hour. Radiation is received through the radiation inlet 312 of the body 310 but is substantially blocked or absorbed before it reaches the radiation outlet 313 of the body 310.

Figure 13A:
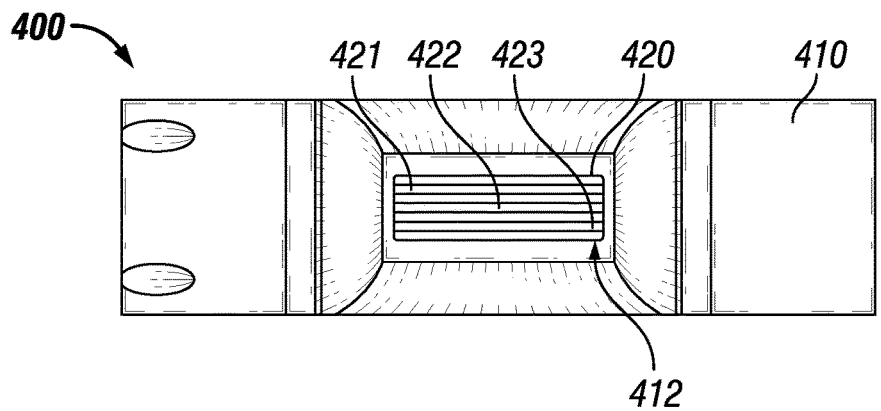
FIG. 13A shows a top view of an embodiment of a shutter having a body and a rotatable member.
Figure 13B:
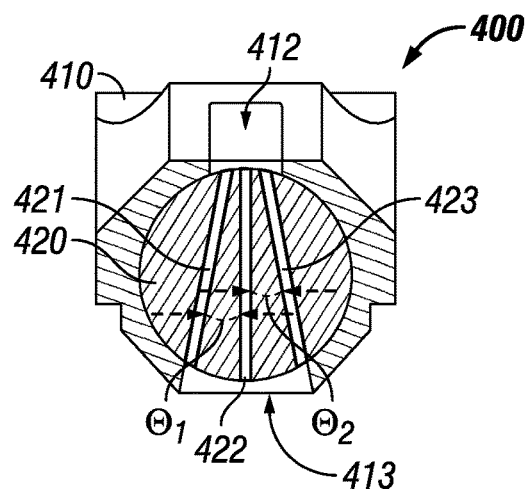
FIG. 13B shows an end cross-sectional view of the embodiment of FIG. 13A.

FIGS. 13A and 13B show an embodiment of a shutter 400 configured to form a plurality of beams 421, 422, 423. The shutter 400 includes a body 410 and a rotatable member 420. The body 410 includes a radiation inlet 412 and a radiation outlet 413. The radiation inlet 412 is configured to receive radiation from a radiation source (not shown in FIGS. 13A and 13B). The radiation outlet 413 of the body 410 may pass all of, or at least a portion of, the radiation received from the rotatable member 420 to a target positioned opposite from the radiation source. The body 410 and rotatable member 420 may be formed of a lead alloy with up to approximately 5% antimony, to add rigidity and hardness. The rotatable member 420 is rotatable about an axis of rotation along the length of the rotatable member 420.

The rotatable member 420 includes a plurality of passageways, such as three passageways 421, 422, 423. Each of the plurality of passageways 421, 422, 423 includes a radiation inlet and a radiation outlet. In some embodiments, the plurality of passageways 421, 422, 423 may share a radiation inlet. Each of the plurality of passageways 421, 422, 423 may be configured to form a collimated beam of radiation. The plurality of passageways 421, 422, 423 may be configured to form beams of different shapes. By way of example, a first passageway 421 and a third passageway 423 may each form a fan beam and a second passageway 422 may form a pencil beam. The plurality of passageways 421, 422, 423 are angularly spaced along the diameter of the rotatable member 420. For example, the second passageway 422 may be aligned with the diameter of the rotatable member 420 as shown. The first passageway 421 may be positioned at a first angle Θ1 from the diameter of the rotatable member 420 and the third passageway 423 may be positioned at a second angle Θ2 from the diameter of the rotatable member 420. Radiation from a radiation source passes though the radiation inlet 412 of the body 410 and into the inlets of the plurality of passageways 421, 422, 423 where it is formed into a plurality of beams. The plurality of beams are then passed through the radiation outlet 413 of the body 410 and toward a target to be irradiated.

The rotatable member 420 may be rotated about its axis of rotation to a closed position. In the closed position, the cross-sectional thickness of the rotatable member 420 between the radiation inlet 412 and the radiation outlet 413 may be such that any radiation that passes through this thickness of the chosen material is reduced to safe continuous exposure levels, such as not to exceed 2 millirem per hour. Radiation is received through the radiation inlet 412 of the body 410 but is substantially blocked or absorbed before it reaches the radiation outlet 413 of the body 410.

Figure 14:
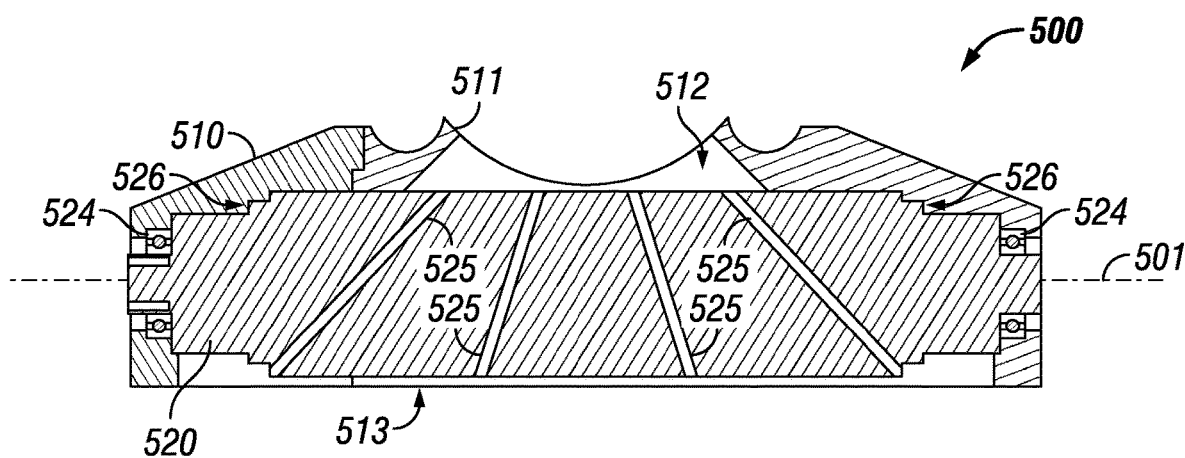
FIG. 14 shows a side cross-sectional view of an embodiment of a shutter having a body and a rotatable member.

FIG. 14 shows an embodiment of a rotatable member 520 configured to selectively form a plurality of pencil beams. The rotatable member 520 may include sleeves or bearings 524 to rotatably support the rotatable member 520 within a body 510. The body 510 and rotatable member 520 may be formed of a lead alloy with up to approximately 5% antimony, to add rigidity and hardness. The body 510 includes a radiation inlet 512 and a radiation outlet 513. The radiation inlet 512 is configured to receive radiation from a radiation source (not shown in FIG. 14). The radiation outlet 513 of the body 510 may pass all of, or at least a portion of, the radiation received from the rotatable member 520 to a target positioned opposite from the radiation source. The rotatable member 520 is rotatable about an axis of rotation 501 along the length of the rotatable member 520. The rotatable member 520 may have a profile with stepped shoulders 526 to increase the points of scatter for scattered radiation energy within a clearance region between the rotatable member 520 and the body 510. The rotatable member 520 includes a plurality of passageways 525 angularly spaced along the length of the rotatable member 520. The plurality of passageways 525 may be configured to form collimated beams of radiation. The plurality of passageways 525 may be configured to form a plurality of pencil beams. Radiation from a radiation source passes though the radiation inlet 512 of the body 510 and into the inlets of the plurality of passageways 521, 522, 523 where it is formed into a plurality of beams. The plurality of beams are then passed through the radiation outlet 513 of the body 510 and toward a target to be irradiated.

The rotatable member 520 may be rotated about its axis of rotation 501 to a closed position. In the closed position, the cross-sectional thickness of the rotatable member 520 between the radiation inlet 512 and the radiation outlet 513 may be such that any radiation that passes through this thickness of the chosen material is reduced to safe continuous exposure levels, such as not to exceed 2 millirem per hour. Radiation is received through the radiation inlet 512 of the body 510 but is substantially blocked or absorbed before it reaches the radiation outlet 513 of the body 510.

A variety of modification and combinations of these embodiments will be understood by those skilled in the art having the benefit of this disclosure. For example, the passageway 422 of the rotatable member 420 (shown in FIG. 13B) may be the plurality of passageways 525 (shown in FIG. 14) and/or the rotatable member 420 may form a plurality of pencil beams between two fan beams. Also for example, a plurality of passageways may be formed between a single radiation inlet and a plurality of radiation outlets, between a plurality of radiation inlets and a plurality of radiation outlets, or combinations thereof. The shapes of the passageways may be configured to form pencil beams, fan beams, other beam shapes, or combinations thereof. Each passageway may direct a respective collimated beam of radiation to a separate portion of a target to be irradiated. For example, at least one beam may be directed forward, at least one beam may be directed backwards, at least one beam may be directed straight down, or combinations thereof. A plurality of passageways may be configured to receive radiation from the radiation source at the same time. A plurality of passageways may be distributed throughout the rotatable member such that rotation of the rotatable member between different open positions aligns different radiation inlets, or subsets of radiation inlets, with the radiation source. For example, a first passageway may form a first fan beam and a second passageway may form a second fan beam that it narrower than the first fan beam. A set of third passageways may form two fan beams. A set of fourth passageways may form a pencil beam between two fan beams.

The plurality of passageways may be angularly spaced along the diameter of the rotatable member, angularly spaced along the length of the rotatable member, or combinations thereof. Each of the plurality of passageways may correspond to an open position where the radiation inlet and the radiation outlet of the passageway is substantially aligned with the center point of the radiation source. The rotatable member may be rotatable between a plurality of open positions to select a beam shape, a beam direction, a plurality of beam shapes, a plurality of beam directions, or combinations thereof. In the closed positions, the thickness and material of the rotatable member may be such that any radiation that passes through this portion of the rotatable member is reduced to safe continuous exposure levels, such as not to exceed 2 millirem per hour.

Although this disclosure has been described in terms of certain preferred embodiments, other embodiments that are apparent to those of ordinary skill in the art, including embodiments that do not provide all of the features and advantages set forth herein, are also within the scope of this disclosure. Accordingly, the scope of the present disclosure is defined only by reference to the appended claims and equivalents thereof.

What is claimed is:

1. A shutter for selectively controlling radiation exposure, the shutter comprising:
 a body; and
 a rotatable member rotatably connected to the body, the rotatable member being rotatable between an open position and a closed position, the open position permitting radiation to pass through the rotatable member, the closed position substantially blocking or absorbing radiation, the rotatable member being configured to collimate the radiation into at least one beam of radiation in the open position, wherein the rotatable member further comprises:

a radiation inlet;
a radiation outlet; and
a passageway extending from the radiation inlet to the radiation outlet, wherein the radiation inlet is positioned to receive radiation when the rotatable member is in the open position, wherein the passageway is shaped to form the radiation into a pencil beam.

2. A shutter for selectively controlling radiation exposure, the shutter comprising:
a body; and
a rotatable member rotatably connected to the body, the rotatable member being rotatable between an open position and a closed position, the open position permitting radiation to pass through the rotatable member, the closed position substantially blocking or absorbing radiation, the rotatable member being configured to collimate the radiation into at least one beam of radiation in the open position, wherein the rotatable member further comprises:
a radiation inlet;
a radiation outlet;
a first passageway extending from the radiation inlet to the radiation outlet, wherein the radiation inlet is positioned to receive radiation when the rotatable member is in the open position;
at least one second radiation inlet;
at least one second radiation outlet; and
a second passageway extending from the at least one second radiation inlet to the at least one second radiation outlet, wherein the radiation inlet and the at least one second radiation inlet are positioned to simultaneously receive radiation when the rotatable member is in the open position.

3. The shutter of claim 2, the body further comprising:
a body radiation inlet;
a body radiation outlet, wherein at least one of the body radiation inlet or the body radiation outlet includes a cover, the cover being transmissive to a portion of radiation; and
a radiation source profile positioned adjacent to the body radiation inlet and configured to receive an exterior surface of a radiation source.

4. The shutter of claim 2, wherein the rotatable member includes a profile having stepped shoulders and is positioned within the body with a clearance region therebetween, the clearance region being configured to provide multiple points of scatter between the rotatable member and the body for scattered radiation energy.

5. The shutter of claim 2, wherein the rotatable member is rotatable about an axis of rotation along a length of the rotatable member, the first passageway and the second passageway are angularly spaced from each other along a diameter of the rotatable member.

6. The shutter of claim 2, wherein the rotatable member is rotatable about an axis of rotation along a length of the rotatable member, the first passageway and the second passageway are angularly spaced along the length of the rotatable member.

7. The shutter of claim 2, wherein the first passageway is shaped to form a first beam shape, the second passageway is shaped to form a second beam shape, the first beam shape being different from the second beam shape.

8. A shutter for selectively controlling radiation exposure, the shutter comprising:
a body comprising:
a body radiation inlet;
a body radiation outlet; and
a radiation source profile positioned adjacent the body radiation inlet and configured to receive an exterior surface of a radiation source, wherein at least one of the body radiation inlet or the body radiation outlet includes a cover, the cover being transmissive to a portion of radiation; and
a rotatable member rotatably connected to the body, the rotatable member being rotatable between an open position and a closed position, the open position permitting radiation to pass through the rotatable member, the closed position substantially blocking or absorbing radiation, the rotatable member being configured to collimate the radiation into at least one beam of radiation in the open position, wherein the rotatable member further comprises:
a radiation inlet;
a radiation outlet; and
a passageway extending from the radiation inlet to the radiation outlet, wherein the radiation inlet is positioned to receive radiation when the rotatable member is in the open position.

9. A shutter for selectively controlling radiation exposure, the shutter comprising:
a rotatable member, the rotatable member being cylindrical and rotatable about an axis of rotation along a length of the rotatable member and having:
at least one passageway configured to collimate radiation into at least one beam of radiation, including a first passageway having a first side, a second side, a radiation inlet, and a radiation outlet, the first passageway extending from the radiation inlet to the radiation outlet, the first side and the second side are at an angle to each other and extend from the radiation inlet to the radiation outlet to form a radiation received into the radiation inlet into a fan beam;
a closed position, wherein the at least one passageway is not positioned to receive radiation when the rotatable member is in the closed position; and
at least one open position including a first open position, wherein the rotatable member is rotatable between the closed position and the at least one open position, the at least one passageway being positioned to receive radiation when the rotatable member is in the at least one open position, the radiation inlet of the first passageway being positioned to receive the radiation when the rotatable member is in the first open position.

10. The shutter of claim 9, wherein the at least one passageway comprises a plurality of passageways including the first passageway and a second passageway.

11. The shutter of claim 10, wherein the first open position permits radiation to simultaneously pass through the first passageway and the second passageway.

12. The shutter of claim 10, wherein the at least one open position comprises a plurality of open positions including the first open position and a second open position, the rotatable member being rotatable between the first open position and the second open position, the first open position permitting radiation to pass through the first passageway, and the second open position permitting radiation to pass through the second passageway.

13. The shutter of claim 9, further comprising a body, the rotatable member is rotatably connected to the body, wherein the rotatable member includes a profile having stepped shoulders and is positioned within the body with a clearance region therebetween, the clearance region being configured to provide multiple points of scatter between the rotatable member and the body for scattered radiation energy.

14. The shutter of claim 9, wherein the at least one passageway comprises a plurality of passageways including the first passageway and at least one second passageway, the rotatable member including a plurality of open positions, each of the plurality of open positions permitting radiation to pass through at least one of the plurality of passageways of the rotatable member, wherein the rotatable member is rotatable between the closed position and the plurality of open positions, the plurality of open positions including the first open position and a second open position, the at least one second passageway is positioned to receive radiation when the rotatable member is in the second open position.

15. The shutter of claim 14, wherein the at least one second passageway comprises a plurality of second passageways, the plurality of second passageways operable to form a plurality of beams of radiation, wherein the rotatable member is rotatable between the first open position and the second open position to select a different number of beams of radiation.

16. The shutter of claim 15, wherein the plurality of second passageways are angularly spaced from each other along a diameter of the rotatable member.

17. The shutter of claim 15, wherein the plurality of second passageways are angularly spaced along the length of the rotatable member.

18. A method of selectively controlling radiation exposure, the method comprising:
    receiving radiation into a shutter having a rotatable member, the rotatable member being cylindrical and rotatable about an axis of rotation along a length of the rotatable member and having at least one passageway configured to collimate radiation into at least one beam of radiation, the at least one passageway including a first passageway having a first side, a second side, a radiation inlet, and a radiation outlet, the first passageway extending from the radiation inlet to the radiation outlet, the first side and the second side are at an angle to each other and extend from the radiation inlet to the radiation outlet to form radiation received into the radiation inlet into a fan beam;
    rotating the rotatable member to a closed position, the closed position substantially blocking or absorbing the radiation; and
    rotating the rotatable member to a first open position, the first open position permitting the radiation to pass through the first passageway and form the fan beam.

19. The method of claim 18, wherein the at least one passageway comprises a plurality of passageways including the first passageway and a second passageway, the second passageway being shaped to form the radiation into a pencil beam, and the method further comprising passing the radiation through the second passageway to form the pencil beam.

20. The method of claim 18, wherein the at least one passageway comprises a plurality of passageways including the first passageway and at least one second passageway, the rotatable member including a plurality of open positions, each of the plurality of open positions permitting radiation to pass through at least one of the plurality of passageways of the rotatable member, wherein the rotatable member is rotatable between the closed position and the plurality of open positions, the plurality of open positions include the first open position and a second open position, and the method further comprising:
    rotating the rotatable member to the second open position, the at least one second passageway receiving the radiation when the rotatable member is in the second open position; and
    collimating the radiation into at least one second beam of radiation when the rotatable member is in the second open position.

21. The method of claim 20, wherein the at least one second passageway comprises a plurality of second passageways, the plurality of second passageways operable to form a plurality of beams of radiation, wherein the rotatable member is rotatable between the first open position and the second open position to select a different number of beams of radiation.

22. The method of claim 18, the rotatable member is rotatably connected to a body, the rotatable member includes a profile having stepped shoulders and is positioned within the body with a clearance region therebetween, the clearance region providing multiple points of scatter between the rotatable member and the body for scattered radiation energy.

* * * * *